United States Patent
Zhang

(10) Patent No.: US 7,744,893 B2
(45) Date of Patent: Jun. 29, 2010

(54) T CELL RECEPTOR CDR3 SEQUENCES ASSOCIATED WITH MULTIPLE SCLEROSIS AND COMPOSITIONS COMPRISING SAME

(75) Inventor: Jingwu Z. Zhang, Missouri City, TX (US)

(73) Assignees: Baylor College of Medicine, Houston, TX (US); Opexa Pharmaceuticals, Inc., Houston, TX (US)

( * ) Notice: Subject to any disclaimer, the term of this patent is extended or adjusted under 35 U.S.C. 154(b) by 1040 days.

(21) Appl. No.: 10/520,296

(22) PCT Filed: Jun. 5, 2003

(86) PCT No.: PCT/US03/17673
§ 371 (c)(1),
(2), (4) Date: Mar. 23, 2006

(87) PCT Pub. No.: WO03/104407
PCT Pub. Date: Dec. 18, 2003

(65) Prior Publication Data
US 2006/0240031 A1    Oct. 26, 2006

Related U.S. Application Data

(60) Provisional application No. 60/386,287, filed on Jun. 5, 2002.

(51) Int. Cl.
*A61K 39/00* (2006.01)
(52) U.S. Cl. .................................. 424/185.1
(58) Field of Classification Search ........................ None
See application file for complete search history.

(56) References Cited

U.S. PATENT DOCUMENTS 5,614,192 A    3/1997   Vandenbark

FOREIGN PATENT DOCUMENTS

| WO | WO 91/15225 A1 | 10/1991 |
| WO | WO 00/50641 A1 | 8/2000 |
| WO | WO 01/42277 * | 6/2001 |

OTHER PUBLICATIONS

Godkins, A.J., et al. J. Immunol. 2001;166:6720-6727.*
Hong J., et al., A Common TCR V-D-J Sequence in Vβ13.1 T Cells Recognizing an Immunodominant Peptide of Myelin Basic Protein in Multiple Sclerosis, Journal of Immunology, 1999;163:3530-8.
Hong, J., et al., Reactivity and Regulatory Properties of Human Anti-Idiotypic Antibodies Induced by T Cell Vaccination, Journal of Immunology, 2000;165:6858-64.
Kozovska, M., et al., T Cell Recognition Motifs of an Immunodominant Peptide of Myelin Basic Protein in Patients with Multiple Sclerosis: Structural Requirements and Clinical Implications, Eur. J. Immunol., 1998;28:1894-1901.
Martin, R., et al., A Myelin Basic Protein Peptide is Recognized by Cytotoxic T Cells in the Context of Four HLA-DR Types Associated with Multiple Sclerosis, Journal of Experimental Medicine, 1991;173:19-24.

* cited by examiner

*Primary Examiner*—G. R Ewoldt
(74) *Attorney, Agent, or Firm*—Todd Lorenz; Rita Wu; Arnold & Porter LLP

(57) ABSTRACT

The present invention relates generally to the field of treating and monitoring multiple sclerosis by utilizing T-cell receptors peptides. In particular, nucleic acids and peptide sequences of T-cell receptors found in a population of MS patients are provided, along with compositions comprising such TCR peptides for use in, e.g., vaccines.

6 Claims, No Drawings

T CELL RECEPTOR CDR3 SEQUENCES ASSOCIATED WITH MULTIPLE SCLEROSIS AND COMPOSITIONS COMPRISING SAME

CROSS REFERENCE TO RELATED APPLICATIONS

This application is the National Stage of International Application Number PCT/US03/17873, filed Jun. 4, 2003, which claims the benefit of U.S. Provisional Application No. 60/386,287, filed Jun. 5, 2002.

FIELD OF THE INVENTION

The present invention relates generally to the field of treatment of autoimmune disease, such as multiple sclerosis (MS). More particularly, it concerns T-cell receptor nucleic acids and peptides found in some MS patients, and methods for detecting the sequences. In addition, the present invention concerns the use of T-cell receptor peptide sequences for the treatment of autoimmune disease, such as MS.

BACKGROUND

Intercellular recognition complexes formed by T cell receptors (TCR) on cytotoxic T lymphocytes or T helper cells and MHC/peptide complexes on antigen presenting cells (APC) are a common recognition component in a diverse set of cell-cell encounters that activate the TCR both during development of the repertoire of T cells within an individual organism (positive selection; negative selection; peripheral survival) and during the control (T helper) and effector stages (T killer) of an adaptive immune response.

In the adaptive immune response, antigens are recognized by hypervariable molecules, such as antibodies or TCRs, which are expressed with sufficiently diverse structures to be able to recognize any antigen. Antibodies can bind to any part of the surface of an antigen. TCRs, however, are restricted to sensing the presence of antigens by binding to short peptides from the antigens that are presented on the surface of APCs bound to class I or class II molecules of the major histocompatibility complex (MHC). TCR recognition of peptide/MHC complexes triggers activation (clonal expansion) of the T cell.

TCRs are heterodimers composed of two chains which can be $\alpha\beta$ (alpha-beta) or $\gamma\delta$ (gamma-delta). The structure of TCRs is very similar to that of immunoglobulins (Ig). Each chain has two extracellular domains, which are immunoglobulin folds. The amino-terminal domain is highly variable and called the variable (V) domain. The domain closest to the membrane is the constant (C) domain. These two domains are analogous to those of immunoglobulins, and resemble Fab fragments. The V domain of each chain has three complementarity determining regions (CDR). Proximal to the membrane, each TCR chain has a short connecting sequence with a cysteine residue that forms a disulfide bond between both chains.

Genes encoding $\alpha\beta$ and $\gamma\delta$ heterodimers are only expressed in the T-cell lineage. The four TCR loci ($\alpha$, $\beta$, $\gamma$, and $\delta$) have a germ-line organization very similar to that of Ig. $\alpha$ and $\gamma$ chains are produced by rearrangements of V and J segments whereas $\beta$ and $\delta$ chains are produced by rearrangements of V, D, and J segments. The gene segments for TCR chains are located on different chromosomes, except the $\delta$-chain gene segments that are between the V and J gene segments of the $\alpha$ chain. The location of $\delta$-chain gene segments has a significance: a productive rearrangement of $\alpha$-chain gene segments deletes C genes of the $\delta$-chain, so that in a given cell the $\alpha\beta$ heterodimer cannot be co-expressed with the $\gamma\delta$ receptor.

In mice, there are about 100 V$\alpha$ and 50 J$\alpha$ genes segments and only one C$\alpha$ segment. The $\delta$-chain gene family has about 10 V, 2 D, and 2 J gene segments. The $\beta$-chain gene family has 20-30 V segments and two identical repeats containing one D$\beta$, six J$\beta$ and one C$\beta$. Finally, the $\gamma$-chain gene family contains 7 V and three different J-C repeats. In humans the organization is similar to that of mice, but the number of segments varies.

The rearrangements of gene segments in $\alpha$ and $\beta$ chains is similar to that of Igs. The $\alpha$ chain, like the light chain of Ig is encoded by V, J, and C gene segments. The $\beta$ chain, like the heavy chain of Ig, is encoded by V, D, and J gene segments. Rearrangements of a chain gene segments result in VJ joining and rearrangements of $\beta$ chain result in VDJ joining. After transcription of rearranged genes, RNA processing, and translation, the $\alpha$ and $\beta$ chains are expressed linked by a disulfide bond in the membrane of T cells.

TCR gene segments are flanked by recognition signal sequences (RSS) containing a heptamer and a nonamer with an intervening sequence of either 12 nucleotides (one turn) or 23 nucleotides (two turn). As in Igs, enzymes encoded by recombination-activating genes (RAG-1 and RAG-2) are responsible for the recombination processes. RAG1/2 recognize the RSS and join V-J and V-D-J segments in the same manner as in Ig rearrangements. Briefly, these enzymes cut one DNA strand between the gene segment and the RSS and catalyze the formation of a hairpin in the coding sequence. The signal sequence is subsequently excised.

The combinatorial joining of V and J segments in a chain and V, D and J segments in $\beta$ chain produces a large number of possible molecules, thereby creating diversity of TCRs. Diversity is also achieved in TCRs by alternative joining of gene segments. In contrast to Ig, $\beta$ and $\delta$ gene segments can be joined in alternative ways. RSS flanking gene segments in $\beta$ and $\delta$ gene segments can generate VJ and VDJ in the $\beta$ chain, and VJ, VDJ, and VDDJ on the $\delta$ chain. As in the case of Ig, diversity is also produced by variability in the joining of gene segments.

Hypervariable loops of the TCR known as complementarity determining regions (CDRs) recognize the composite surface made from a MHC molecule and a bound peptide. The CDR2 loops of $\alpha$ and $\beta$ contact only the MHC molecule on the surface of APC, while the CDR1 and CDR3 loops contact both the peptide and MHC molecule. Compared with Ig, TCRs have more limited diversity in the CDR1 and CDR2. However, diversity of CDR3 in TCRs is higher than that of Ig, because TCRs can join more than one D segment leading to augmented junctional diversity.

The pathogenesis of a number of autoimmune diseases is believed to be caused by autoimmune T cell responses to self-antigens present in the organism. Not all autoreactive T cells are deleted in the thymus, in contradiction with the clonal selection paradigm. Those T cells with TCRs for a broad spectrum of self-antigens represent part of the normal T-cell repertoire and naturally circulate in the periphery. It is unclear why autoreactive T cells are allowed, during their evolution, to undergo differentiation in the thymus and are accommodated in the periphery. While their physiological role is not understood, these autoreactive T cells, when activated, present a potential risk in the induction of autoimmune pathologies. Autoreactive T cells can also be isolated from normal individuals without the consequences of autoimmune diseases. It has been established that antigen recognition of autoreactivity by itself is not sufficient to mediate the autodestructive process. One of the prerequisites for autoreactive T cells to be pathogenic is that they must be activated.

Autoreactive T cells are indicated in the pathogenesis of autoimmune diseases, such as multiple sclerosis (MS) and rheumatoid arthritis (RA). The pathogenesis of autoreactive T cells in MS is generally held to arise from T cell responses to myelin antigens, in particular myelin basic protein (MBP). MBP-reactive T cells are found to undergo in vivo activation, and occur at a higher precursor frequency in blood and cerebrospinal fluid in patients with MS as opposed to control individuals. These MBP-reactive T cells produce Th1 cytokines, e.g. IL-2, TNF, and γ-interferon, which facilitate migration of inflammatory cells into the central nervous system and exacerbate myelin-destructive inflammatory responses in MS.

MBP-reactive T cells have also been shown to be involved in the pathogenesis of experimental autoimmune encephalomyelitis (EAE) in animals, which resembles multiple sclerosis. EAE can be induced actively in susceptible animals by injecting MBP emulsified in an adjuvant or passively by injecting MBP-reactive T-cell lines and clones derived from MBP-sensitized animals. When activated in vitro, very small numbers of MBP-reactive T cells are required to induce EAE, while 100-fold more resting T cells with the same reactivity are incapable of mediating the diseases.

It has been demonstrated that vaccination with inactivated MBP-reactive T cells depletes MBP-reactive T cells in EAE, a procedure called T-cell vaccination, which has been used to prevent and to treat EAE. Ben-Nun et al., Nature 292: 60-61 (1981). Although the mechanism underlying T cell vaccination is not completely understood, it is thought to involve the idiotypic regulatory networks through interactions with the TCR and the so-called anti-ergotypic T cell responses that react presumably with the T cell activation markers. The idiotypic and anti-ergotypic regulatory networks are believed to be essential for the protective immunity induced by T cell vaccination, because the protective immunity conferred by T cell vaccination is specific for the disease that autoimmune T cells used for vaccination are able to induce. In addition, anti-idiotypic T cells isolated form immunized rodents specifically recognize the immunizing T cell clones/lines but not T cells expressing distant TCR structural features. It is believed that TCR determinants recognized by anti-idiotypic T cells most likely reside within CDR3 or CDR2, as predicted by characteristic sequence diversity within these regions.

In EAE, encephalitogenic MBP-reactive T cells are restricted to very limited epitopes on MBP. These restrictions in the diversity of the pathogenic T-cell responses permit specific immune intervention. Various therapeutic strategies have been designed accordingly to target the Vβ region of the TCR in preventing the development of EAE in sensitized animals. For example, monoclonal antibodies have been targeted to the Vβ gene product and peptide vaccines have been based on the CDR2 region of the responsible Vβ gene.

Some of the studies on EAE have been extended to human autoimmune diseases. For instance, a peptide corresponding to TCR Vβ 5.2 has been used in clinical trials to treat patients with MS and a Vβ 14 peptide has been used to vaccinate patients with RA. U.S. Pat. No. 5,614,192 (Vandenbark) discloses treatment of autoimmune diseases by the use of immunogenic TCR peptides of 15 to 30 amino acids comprising at least part of CDR2. U.S. Pat. No. 6,303,314 (Zhang) discloses the treatment of autoimmune diseases by using certain immunogenic TCR peptides in combination with immunogenic T cell activation marker peptides.

One area in which vaccination with TCR peptides can be improved is by determining which, if any, common motifs are found in the autoreactive TCRs of a patient with an autoimmune disease such as MS. Such common motifs can be used either as a basis for a peptide vaccine to activate an anti-idiotypic immune response in MS patients for the purpose of depleting T cells which have TCRs comprising said motifs, or as a target for the preparation of antibodies that can functionally block or directly deplete T cells which have TCRs comprising said motifs.

Therefore, it is desirable to determine the amino acid sequences of common motifs specifically found in the TCRs of autoreactive T cells from patients with autoimmune diseases. It is also desirable to be able to readily detect such motifs in a patient sample by a convenient method, such as PCR. In addition, it is desirable to use peptides identical to or derived from the detected motifs to treat patients with the autoimmune disease. It is also desirable to use antibodies which specifically bind to said motifs to treat a patient with an autoimmune disease.

U.S. Pat. No. 6,303,314 (Zhang) discloses such a common motif found in the TCRs of a subset of Vβ13.1 T cells, the "LGRAGLTY motif", which has the amino acid sequence Leu Gly Arg Ala Gly Leu Thr Tyr (SEQ ID NO:10), as well as a method for its ready detection by PCR. This motif is found in some TCRs of some autoreactive T cells that recognize amino acids 83-99 of MBP (hereinafter "MBP83-99"). Peptides based on the LGRAGLTY motif can be used to vaccinate some patients in order to treat or prevent autoimmune diseases with which Vβ13.1-LGRAGLTY is associated (e.g., MS).

As the LGRAGLTY motif is present in only some TCRs that recognize MBP83-99, there remains a need to identify other TCR sequences and more particularly CDR sequences commonly expressed by MBP-reactive T cells. In addition, there remains a need to be able to detect other TCR sequences, including CDR sequences, which are commonly expressed by MBP-reactive T cells. Finally, there remains a need to develop treatments for autoimmune diseases associated with other TCR sequences, and more particularly CDR sequences.

DETAILED DESCRIPTION

To aid in the understanding of the present invention, several terms are defined below.

"PCR" means the polymerase chain reaction, for example, as generally described in U.S. Pat. No. 4,683,202 (issued Jul. 28, 1987 to Mullis), which is incorporated herein by reference. PCR is an amplification technique wherein selected oligonucleotides, or primers, may be hybridized to nucleic acid templates in the presence of a polymerization agent (such as a DNA or RNA polymerase) and nucleotide triphosphates, whereby extension products may be formed from the primers. These products may then be denatured and used as templates in a cycling reaction that amplifies the number and amount of existing nucleic acids which may facilitate their subsequent detection. A variety of PCR techniques are known in the art and may be used in connection with the disclosure herein.

"Peptide" means a peptide, whether natural, synthetic, or a modification thereof, capable of eliciting an immune response to a specific peptide or polypeptide sequence.

"Primer" means an oligonucleotide, whether natural, synthetic, or a modification thereof, capable of acting as a point of initiation of nucleotide synthesis sufficiently complementary to a specific nucleotide sequence on a template molecule.

"Probe" means an oligonucleotide, whether natural, synthetic, or a modification thereof, capable of specifically binding to a sufficiently complementary nucleotide sequence.

"Derived from," in the context of nucleotide sequences means that the nucleotide sequence is not limited to the specific sequence described, but also includes variations in that sequence, which may include nucleotide additions, deletions, substitutions, or modifications to the extent that the variations to the described sequence retain the ability to specifically bind to the complement of the described sequence. In the context of peptide or polypeptide sequences, "derived from" means that the peptide or polypeptide is not limited to the specific sequence described, but also includes variations in that sequence, which may include amino acid additions, deletions, substitutions, or modifications to the extent that the variations in the listed sequences retain the ability to elicit an immune response to the described sequence.

"Immunogenic," when used to describe a peptide or polypeptide, means the peptide or polypeptide is able to induce an immune response, either T cell mediated, antibody, or both. "Antigenic" means the peptide or polypeptide may be recognized in a free form by antibodies and/or in the context of MHC molecules in the case of antigen-specific T cells.

"Immune-related disease" means a disease in which the immune system is involved in the pathogenesis of the disease. A subset of immune-related diseases are autoimmune diseases. Autoimmune diseases include, but are not limited to, rheumatoid arthritis, myasthenia gravis, multiple sclerosis, systemic lupus erythematosus, autoimmune thyroiditis (Hashimoto's thyroiditis), Graves' disease, inflammatory bowel disease, autoimmune uveoretinitis, polymyositis, and certain types of diabetes. In view of the present disclosure, one skilled in the art can readily perceive other autoimmune diseases treatable by the compositions and methods of the present invention.

"T cell mediated disease" means a disease arising as a result of T cells recognizing peptides normally found in the organism.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

In a first aspect, the present invention is directed to a peptide comprising about 4 to 20 amino acids in length, comprising at least 4 contiguous amino acids of SEQ ID NOS: 4, 5 or 6, or sequences derived therefrom. The peptide may also be about 4 to 12 amino acids in length, comprising either (i) 4, 5, 6 or 7 contiguous amino acids of SEQ ID NOS: 4 or 6, or sequences derived therefrom, (ii) 4, 5, 6, 7 or 8 contiguous amino acids of SEQ ID NO: 5, or sequences derived therefrom. The peptide may also be about 4 to 20 amino acids in length, comprising the sequences of SEQ ID NOS: 4, 5 or 6, or sequences derived therefrom. The peptide may be natural, synthetic, or derived therefrom.

The peptide may be used as an antigen to elicit an immune response to a peptide or polypeptide comprising SEQ ID NOS: 4, 5 or 6, or sequences derived therefrom. As more fully described below, an immune response elicited by the peptide may be used as a basis for treatment, the production of antibodies, the purification of antibodies, and in diagnostic assays.

The peptide may be covalently modified in a number of ways known to those skilled in the art. Selected side chains or terminal residues of the peptide may be modified using common derivatizing agents.

Cysteine residues may be reacted with α-haloacetates (and corresponding amines), such as chloroacetic acid or chloroacetamide, to give carboxymethyl or carboxyamidomethyl derivatives. Cysteine residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidine residues may be derivatized by reaction with the histidine-specifc reagent diethylprocarbonate at pH 5.5-7.0. Para-bromophenacyl bromide may also be used in 0.1M sodium cacodylate at pH 6.0.

Lysine and amino terminal residues may be reacted with succinic or other carboxylic acid anhydrides. Derivatization with these agents may have the effect of reversing the charge of the lysine residues. Other reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginine residues may be modified by reaction with one or several conventional reagents, among them phenylglyoxal, 2,3-butanedione, 1,2-cyclohexanedione, and ninhydrin. Derivatization of arginine residues may be performed in alkaline conditions because of the high $pK_a$ of the guanidine functional group. Furthermore, these reagents may react with the groups of lysine as well as the arginine epsilon-amino group.

Tyrosine residues may be reacted with aromatic diazonium compounds or tetranitromethane. N-acetylimidizol and tetranitromethane may be used to form O-acetyl tyrosyl species and 3-nitro derivatives, respectively. Tyrosine residues may be iodinated using $^{125}I$ or $^{131}I$ to prepare labeled proteins for use in radioimmunoassays.

Carboxyl side groups of aspartic acid and glutamic acid may be modified by reaction with carbodiimides (R'—N—C—N—R') such as 1-cyclohexyl-3-(2-morpholinyl-(4 ethyl) carbodiimide or 1-ethyl-3 (4 azonia 4,4-dimethylpentyl)carbodiimide. Furthermore, aspartyl and glutamyl residues may be converted to asparaginyl and glutaminyl residues by reaction with ammonium ions. Glutaminyl and asparaginyl residues may be deamidated to the corresponding glutamyl and aspartyl residues. Alternatively, these residues may be deamidated under mildly acidic conditions.

Derivatization of the peptide with bifunctional agents may be useful for cross-linking the peptide to a water-insoluble support matrix or to other macromolecular carriers. Commonly used cross-linking agents include, but are not limited to, 1,1-bis(diazoacetyl)-2-phenylethane, glutaraldehyde, N-hydroxysuccinimide esters, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophanyl)dithio]propioimidate may yield photoactivatable intermediates that are capable of crosslinking in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

The peptide may also be modified by hydroxylation of proline and lysine residues, phosphorylation of hydroxyl groups of serine or threonine residues, methylation of the α-amino groups of lysine, arginine, and histidine side chains (T. E. Creighton, Proteins: Structure and Molecule Properties, W. H. Freeman & Co., San Francisco, pp. 79-86 (1983)), acetylation of the N-terminal amine, and, in some instances, amidation of the C-terminal carboxyl groups.

Derivatization of the peptide may improve the peptide's solubility, absorption, biological half life, and the like. Derivatization may also eliminate or attenuate any undesirable side effect of the peptide and the like, as disclosed in Remington's Pharmaceutical Sciences, 16th ed., Mack Publishing Co., Easton, Pa. (1980), which is hereby incorporated by reference. Chemical modification of the peptide may provide additional advantages under certain circumstances, such as increasing the stability and circulation time of the peptide and increasing immunogenicity. For more information on the chemical derivatization of peptides, see U.S. Pat. No. 6,350,730 (Friedman), which is hereby incorporated in its entirety.

The immunogenicity of the peptide may be enhanced by including the peptide in a longer peptide or polypeptide or by conjugating the peptide to "immunological" carriers, such as KLH, serum albumin, tetanus toxoid, and the like, using standard linking techniques. A variety of such methods is known in the art, e.g., use of condensing agents such as dicyclohexylcarbodiimide or use of linkers, such as those commercially available from Pierce Chemical Co., Rockford, Ill.

The peptide may also be formulated for intraarterial, intraperitoneal, intramuscular, subcutaneous, intravenous, oral, nasal, rectal, buccal, intracisternal, intrathecal, sublingual, pulmonary, topical, transdermal, or other routes of administration.

The peptide may also be used to activate T cells with TCRs that specifically bind to peptides orpolypeptides comprising SEQ ID NOS: 4, 5 or 6, or sequences derived therefrom. T cells may be obtained from a patient with an autoimmune disease using any of a number of methods known in the art. The T cells may also be enriched for a particular subpopulation, such as autoreactive T cells. The isolated T cells may then be stimulated with the peptide in vitro, which may activate and/or expand the number of T cells with TCRs that specifically bind to peptides or polypeptides comprising SEQ ID NOS: 4, 5 or 6, or sequences derived therefrom. The activated and/or expanded T cells may then be administered to the patient from which the T cells were derived, whereby they may bind to autoreactive T cells with TCRs comprising SEQ ID NOS: 4, 5 or 6, or sequences derived therefrom, thereby depleting said autoreactive T cells.

In a second aspect, the present invention is directed to an antibody which specifically binds to an epitope comprising a sequence of SEQ ID NOS: 4, 5 or 6, or sequences derived therefrom. The antibody may be of classes IgG, IgM, IgA, IgD, and IgE, and fragments and derivatives thereof, including Fab, F(ab')2, Fd, and single chain antibodies (scFv). The antibody may be a monoclonal antibody, polyclonal antibody, affinity purified antibody, or mixtures thereof which exhibits sufficient binding specificity to an epitope comprising a sequence of SEQ ID NOS: 4, 5 or 6, or sequences derived therefrom. The antibody may be derivatized by the attachment of one or more chemical, peptide, or polypeptide moieties known in the art, as described above in the first aspect of the present invention.

The antibody may be identified and isolated by using techniques known in the art, such as phage display, as described in U.S. Pat. No. 5,565,332 (Hoogenboom et al.), U.S. Pat. No. 5,858,657 (Winter et al.), U.S. Pat. No. 5,871,907 (Winter et al.), U.S. Pat. No. 5,969,108 (McCafferty et al.), and U.S. Pat. No. 6,172,197 (McCafferty et al.), which are hereby incorporated in their entirety. The antibody may also be isolated from a mammal including, but not limited to, mice, rat, goat, rabbit, sheep, porcine or bovine immunized with an antigen capable of eliciting an immune response to a sequence of SEQ ID NOS: 4, 5 or 6, or sequences derived therefrom. The antibody may also be a human or humanized antibody, as described in U.S. Pat. No. 5,565,332 (Hoogenboom et al.), U.S. Pat. No. 5,858,657 (Winter et al.), U.S. Pat. No. 5,871,907 (Winter et al.), U.S. Pat. No. 5,969,108 (McCafferty et al.), and U.S. Pat. No. 6,172,197 (McCafferty et al.), which are hereby incorporated in there entirety.

As more fully described below, the antibody may be used as a basis for treatment or in diagnostic assays. The antibody may also be used for the enrichment or purification of autoreactive T cells which have TCRs comprising a sequence of SEQ ID NOS: 4, 5 or 6, or sequences derived therefrom. Enriched or purified autoreactive T cells which have TCRs comprising SEQ ID NOS: 4, 5 or 6, or sequences derived therefrom, may be used in a T cell vaccine for a patient with an autoimmune disease according to copending U.S. patent application Ser. No. 09/952,532 (Zhang), which is hereby incorporated in its entirety.

In a third aspect, the present invention is directed to an oligonucleotide that encodes a peptide or polypeptide comprising a peptide according to the first exemplary invention, or a fragment thereof. The oligonucleotide may be about 15 to 30 nucleotides in length, comprising at least 10 contiguous nucleotides encoding a fragment of SEQ ID NOS: 4, 5 or 6, the nucleotide sequences complementary thereto, or sequences derived therefrom. The oligonucleotide may also be about 15 to 30 nucleotides in length, comprising either (i) 11, 12, 13, 14, 15, 16, 17, 18, 19 or 20 contiguous nucleotides encoding a fragment of SEQ ID NOS: 4 or 6, the nucleotide sequences complementary thereto, or sequences derived therefrom, (ii) 11, 12, 13, 14, 15, 16, 17, 18, 19, 20 21, 22, 23, 24, 25 or 26 contiguous nucleotides encoding a fragment of SEQ ID NO: 5, the nucleotide sequence complementary thereto, or sequences derived therefrom. The oligonucleotide may also be about 15 to 30 nucleotides in length, comprising a nucleotide sequence encoding SEQ ID NOS: 4, 5 or 6, the nucleotide sequences complementary thereto, or sequences derived therefrom.

Due to the degeneracy of the genetic code, a number of nucleotide sequences may encode the peptide of the first aspect of the present invention. For example, the oligonucleotide may be about 15 to 30 nucleotides in length, comprising at least 10 contiguous nucleotides of SEQ ID NOS: 1, 2 or 3, the sequences complementary thereto, or sequences derived therefrom. The oligonucleotide may also be about 15 to 30 nucleotides in length, comprising either (i) 11, 12, 13, 14, 15, 16, 17, 18, 19 or 20 contiguous nucleotides of SEQ ID NOS: 1 or 3, the sequences complementary thereto, or the sequences derived therefrom, (ii) 11, 12, 13, 14, 15, 16, 17, 18, 19, 20 21, 22, 23, 24, 25 or 26 contiguous nucleotides of SEQ ID NO: 2, the sequences complementary thereto, or the sequences derived therefrom. The oligonucleotide may also be about 15 to 30 nucleotides in length, comprising a nucleotide sequence of SEQ ID NOS: 1, 2 or 3, the sequences complementary thereto, or the sequences derived therefrom.

As more fully described below, the oligonucleotide may be used as primer for PCR. The oligonucleotide may also be used as a probe to bind to, and also detect, a TCR gene, or fragment thereof, which comprises a complementary nucleotide sequence or a nucleotide sequence derived therefrom. The oligonucleotide may be labeled with a detectable moiety. Many examples of detectable moieties are known in the art including, but not limited to, $^{32}P$, $^{35}S$, biotin or digoxigenin.

In a fourth aspect, the present invention is directed to a primer pair comprising a first primer which is an oligonucleotide according to the third aspect of the present invention and a second primer which is an oligonucleotide of about 15 and 30 nucleotides in length that does not comprise a sequence of the first primer and is a fragment of the region from Vβ to Cβ of the TCR gene in T cells, or sequences derived therefrom, wherein the first and second primers specifically bind to different strands of the TCR gene. The second primer may be complementary to a sequence of the Cβ region such that approximately 400 bp, including the Vβ-Dβ-Jβ region of the TCR gene, separate the first and second primers.

As more fully described below, the primer pair may be used to amplify a nucleotide sequence encoding a TCR from a human T cell comprising the sequence of SEQ ID NOS: 4, 5 or 6, or sequences derived therefrom.

In a fifth aspect, a TCR comprising a sequence of SEQ ID NOS: 4, 5 or 6, or sequences derived therefrom, may be detected in a sample by performing an immunoassay using an antibody according to the second aspect of the present invention. By the term "immunoassay," it is meant to include simultaneous sandwich, forward sandwich and reverse sandwich immunoassays, which are well understood to those skilled in the art.

The sample to be tested for the presence of a TCR comprising a sequence of SEQ ID NOS: 4, 5 or 6, or sequences derived therefrom, may be isolated, directly or indirectly, from any animal or human tissue that expresses T cell receptor β chain genes, such as peripheral blood mononuclear cells (PBMC).

In a sixth aspect, a TCR gene comprising a nucleotide sequence encoding SEQ ID NOS: 4, 5 or 6, or sequences derived therefrom (the "Target Sequence"), may be detected in a sample by amplifying a fragment of the TCR gene comprising the Target Sequence, wherein said amplification is performed using a primer pair according to the fourth aspect of the present invention.

The fragment of a TCR gene comprising the Target Sequence encoding SEQ ID NOS: 4, 5 or 6, or sequences derived therefrom, may be amplified by the polymerase chain reaction (PCR) using any particular PCR technique or equipment known in the art. For example, PCR amplification may follow a procedure wherein a reaction mixture is prepared that contains the following ingredients: 5 μL 10×PCR buffer II (100 mM Tris-HCl, pH 8.3, 500 mM KCl), 3 μL 25 mM $MgCl_2$, 1 μL 10 mM dNTP mix, 0.3 μL Taq polymerase (5 U/μL) (AmpliTaq Gold, Perkin Elmer, Norwalk, Conn.), 30 pmol of a first primer, 30 pmol of a second primer, and 1 μL of sample DNA. The polymerase may be stable at temperatures of at least 95° C., have a processivity of 50-60 and have an extension rate of greater than 50 nucleotides per minute.

The PCR reaction may be performed with an amplification profile of 1 min at 95° C. (denaturation), 20 sec at 56° C. (annealing), and 40 sec at 72° C. (extension) for a total of 40 cycles. Before the first cycle begins, the reaction mixture may undergo an initial denaturation for a period of about 5 min to 15 min. Similarly, after the final cycle is complete, the reaction mixture may undergo a final extension for a period of about 5 min to 10 min. Certain PCR reactions may work with as few as 15 to 20 cycles or as many as 50 cycles. Depending upon the specific PCR reaction, longer or shorter incubation times and higher or lower temperatures for each step of the amplification profile may be used.

The sample to be tested for the presence of a TCR gene comprising the Target Sequence, may be a nucleic acid, such as genomic DNA, cDNA, DNA previously amplified by PCR, or any other form of DNA. The sample may be isolated, directly or indirectly, from any animal or human tissue that expresses T cell receptor β chain genes, such as peripheral blood mononuclear cells (PBMC). Genomic DNA may be isolated directly from a tissue that expresses T cell receptor β chain genes. cDNA may be isolated indirectly by reverse transcription of mRNA directly isolated from a tissue that expresses T cell receptor β chain genes.

The ability to detect the presence of a T cell receptor gene comprising a nucleotide sequence encoding SEQ ID NOS: 4, 5 or 6, or sequences derived therefrom, may be enhanced by isolating the sample DNA indirectly by amplification of genomic DNA, cDNA, or any other form of DNA, by a two-step PCR reaction. For example, a first PCR amplification reaction may be performed to amplify a preliminary fragment that is larger than, and comprises, a fragment to which the first and second primers are capable of selectively binding on opposite strands. A second PCR amplification reaction may then be performed, using the preliminary fragment as a template with the first and second primers, to amplify a fragment comprising the Target Sequence. If either the first or second primer is used in the first PCR reaction to amplify the preliminary fragment, the second PCR reaction is "semi-nested." If neither the first or second primer is used in the first PCR reaction to amplify the preliminary fragment, the second PCR reaction is "nested."

In an exemplary two-step PCR reaction, a fragment of a TCR gene comprising a nucleotide sequence encoding SEQ ID NOS: 4, 5 or 6, or sequences derived therefrom, may be amplified by performing a first PCR reaction using a first preliminary primer that anneals to the Vβ region of the TCR gene and a second preliminary primer that anneals to the Cβ region of the TCR gene, which amplifies a preliminary fragment that extends from Vβ through the Vβ-Dβ-Jβ junction to Cβ, followed by a second PCR reaction which may be nested or semi-nested. In light of the present disclosure, the skilled artisan will be able to select appropriate primers and reaction conditions for PCR amplification of a fragment of a TCR gene from T cells comprising a nucleotide sequence encoding SEQ ID NOS: 4, 5 or 6, or sequences derived therefrom.

After amplification of a fragment of a TCR gene comprising a nucleotide sequence encoding SEQ ID NOS: 4, 5 or 6, or sequences derived therefrom, the amplified product may be detected by a number of procedures. For example, an aliquot of amplification product may be loaded onto an electrophoresis gel, to which an electric field is applied to separate DNA molecules by size. In another method, an aliquot of amplification product may be loaded onto a gel stained with SYBR green, ethidium bromide, or another molecule that will bind to DNA and emit a detectable signal. A dried gel may contain a labeled oligonucleotide according to the third aspect of the present invention, from which an autoradiograph may be taken by exposing the gel to film.

In a seventh aspect of the present invention, a test kit comprises an antibody according to the second aspect of the present invention. The test kit may be used to assay a sample for the presence of a TCR, or a derivative thereof, comprising a sequence of SEQ ID NOS: 4, 5 or 6, or sequences derived therefrom.

The test kit may also comprise one or more additional antibodies that specifically bind to an epitope of a TCR on autoreactive T cells. The TCR to which said one or more additional antibodies specifically bind may either comprise or not comprise a sequence of SEQ ID NOS: 4, 5 or 6, or sequences derived therefrom. As a sequence of SEQ ID NOS: 4, 5 or 6, or sequences derived therefrom, is present in only some TCRs, it may prove beneficial to use antibodies that bind to other TCR sequences and more particularly other CDR sequences.

The test kit may also further comprise one or more reagents that may be used in the detection of a TCR, or derivative thereof, comprising a sequence of SEQ ID NOS: 4, 5 or 6, or sequences derived therefrom. The reagent may be a buffer, a positive control, a negative control, or combinations thereof. The positive control may be a peptide or polypeptide sequence comprising a sequence of SEQ ID NOS: 4, 5 or 6, or sequences derived therefrom. The negative control may be a peptide or polypeptide sequence comprising a sequence which does not comprise a sequence of SEQ ID NOS: 4, 5 or 6, or sequences derived therefrom.

In an eighth aspect of the present invention, a test kit comprises a first primer which is an oligonucleotide according to the third aspect of the present invention. The test kit may also comprise a first and second primer, which is a primer pair according to the fourth aspect of the present invention.

The test kit may also further comprise one or more reagents that may be used in the amplification of a fragment of a TCR gene comprising a nucleotide sequence encoding SEQ ID NOS: 4, 5 or 6, or sequences derived therefrom. The reagent may be a buffer, deoxynucleotide triphosphates, heat-stable DNA polymerase, a positive control, a negative control, or combinations thereof. The heat-stable DNA polymerase may be Taq polymerase. The positive control may be a nucleotide sequence comprising a nucleotide sequence encoding SEQ ID NOS: 4, 5 or 6, or sequences derived therefrom. The negative control may be a nucleotide sequence which does not comprise a nucleotide sequence encoding SEQ ID NOS: 4, 5 or 6, or sequences derived therefrom. The test kit may also comprise a labeled oligonucleotide as described in the third aspect of the present invention. Other reagents that may be included in the test kit are known to one skilled in the art.

In an ninth aspect, a patient with an autoimmune disease may be diagnosed by obtaining a sample from a patient, and assaying said sample for the presence of autoreactive T cells comprising a TCR comprising a sequence of SEQ ID NOS: 4, 5 or 6, or sequences derived therefrom. The sample may be enriched for T cells, autoreactive T cells, or autoreactive MBP83-99 T cells. The autoimmune disease may be any autoimmune disease in which TCRs comprising a peptide sequence of SEQ ID NOS: 4, 5 or 6, or sequences derived therefrom, are found on T cells.

The autoimmune disease may be diagnosed by comparing the level of T cells comprising TCRs comprising a sequence of SEQ ID NOS: 4, 5 or 6, or sequences derived therefrom, with the level of said T cells from controls. The level of T cells may be determined by detecting the presence of TCRs comprising a sequence of SEQ ID NOS: 4, 5 or 6, or sequences derived therefrom, in an immunoassay according to the fifth aspect of the present invention. The level of T cells may also be determined by detecting the presence of a nucleic acid encoding a sequence comprising SEQ ID NOS: 4, 5 or 6, or sequences derived therefrom, using PCR in the manner described in the sixth aspect of the present invention.

In a tenth aspect, an autoimmune disease may be treated in some patients with autoreactive T cells comprising TCRs comprising a sequence of SEQ ID NOS: 4, 5 or 6, or sequences derived therefrom, by administering a vaccine comprising an immunogenically effective amount of a peptide according to the first aspect of the present invention. Administration of the vaccine may lead to an immune response, wherein the patient may develop antibodies and which may also induce a T cell response that recognize and bind to the TCRs comprising a sequence of SEQ ID NOS: 4, 5 or 6, or sequences derived therefrom, which may lead to depletion of said autoreactive T cells.

The vaccine may comprise the peptide alone, or in combination with immunogenically effective amounts of other TCR peptide sequences, particularly other CDR sequences. Clinical studies indicate that autoimmune patients receiving autologous T cell vaccination may show a gradual decline in the immunity against MBP-reactive T cells. In some cases, the reappearing autoreactive T cells may originate from different clonal populations, suggesting that MBP-reactive T cells may undergo clonal shift or epitope spreading potentially associated with the ongoing disease process. Clonal shift or epitope spreading may be a problem in autoimmune diseases mediated by autoreactive T cells. A vaccine comprising multiple antigenic peptides capable of inducing an immune response to TCRs on multiple populations of autoreactive T cells may avoid problems with clonal shift or epitope spreading.

Because TCRs comprising a sequence of SEQ ID NOS: 4, 5 or 6, or sequences derived therefrom, as well as other TCR sequences, particularly CDR sequences, may be present in both patients suffering from an autoimmune disease and normal individuals who are not suffering from the disease, a vaccine comprising a peptide or combination of peptides capable of eliciting an immune response to epitopes on TCRs, particularly CDRs and most particularly CDR3, may be able to be administered to both patients with an autoimmune disease and normal individuals. Other peptide sequences may include the LGRAGLTY motif (SEQ ID NO: 7) and CDR sequences disclosed in U.S. Pat. No. 5,614,192 (Vandenbark)

The vaccine may further comprise a T cell activation marker peptide. The T cell activation marker peptide may be a marker peptide as described in U.S. Pat. No. 6,303,314 (Zhang), which is incorporated herein by reference. The vaccine may also further comprise one or more reagents that may be used to enhance the immune response to the immunogen. The reagent may be a buffer, adjuvant or a combination thereof. The adjuvant may be a chitosan-based adjuvant according to U.S. Pat. No. 5,980,912 (Podolski), which is hereby incorporated by reference in its entirety.

In an eleventh aspect, an autoimmune disease may be treated in some patients with TCRs comprising a sequence of SEQ ID NOS: 4, 5 or 6, or sequences derived therefrom, by administering a composition comprising an antibody according to the second aspect of the present invention. Administration of the composition may lead to depletion of TCRs which comprise a sequence of SEQ ID NOS: 4, 5 or 6, or sequences derived therefrom.

The composition may comprise the antibody alone, or in combination with other antibodies which specifically bind to other TCR sequences, particularly other CDR sequences. As discussed above, the progression of an autoimmune disease may include clonal shift or epitope spreading of autoreactive T cells. A composition comprising multiple antibodies wherein each antibody specifically binds to a different epitope of TCRs, particularly a CDR, on multiple populations of autoreactive T cells may avoid problems with clonal shift or epitope spreading.

Because TCRs comprising a sequence of SEQ ID NOS: 4, 5 or 6, or sequences derived therefrom, as well as other TCR sequences, particularly CDR sequences, may be present in both patients suffering from an autoimmune disease and normal individuals who are not suffering from the disease, a composition comprising an antibody or combination of antibodies that specifically bind to epitopes on TCRs, particularly CDRs and most particularly CDR3, may be able to be administered to both patients with an autoimmune disease and normal individuals.

In a twelfth aspect of the present invention, an autoimmune disease may be monitored by detecting the presence of a TCR gene comprising the sequence of SEQ ID NOS: 1, 2 or 3, or sequences derived therefrom, in a sample from a patient with an autoimmune disease in accordance with the sixth aspect of the present invention, and quantifying the amount of the TCR gene comprising the sequence of SEQ ID NOS: 1, 2 or 3, or sequences derived therefrom.

The severity of symptoms of the autoimmune disease may correlate with the amount of detected DNA in the sample by virtue of the number of autoreactive T cells. In addition, an increase in the amount of detected DNA in the sample may be used as an indication to apply treatments intended to minimize the severity of the symptoms and/or treat the disease before the symptoms appear.

In an thirteenth aspect of the present invention, an autoimmune disease may be monitored by detecting the presence of TCRs comprising the sequence of SEQ ID NOS: 4, 5 or 6, or sequences derived therefrom, in a sample from a patient with an autoimmune disease in accordance with the seventh aspect of the present invention, and quantifying the amount of TCRs comprising the sequence of SEQ ID NOS: 4, 5 or 6, or sequences derived therefrom.

The severity of symptoms of the autoimmune disease may correlate with the amount of detected peptide or polypeptide in the sample by virtue of the number of autoreactive T cells. In addition, an increase in the amount of detected peptide or polypeptide in the sample may be used as an indication to apply treatments intended to minimize the severity of the symptoms and/or treat the disease before the symptoms appear.

In a fourteenth aspect, the present invention is directed to the manufacture of pharmaceutical compositions, such as a vaccine described in the tenth aspect of the present invention and the antibody described in the eleventh aspect of the present invention. The pharmaceutical composition may be produced using methods well known in the art.

Pharmaceutical compositions used as preclinical and clinical therapeutics in the treatment of disease or disorders may be produced by those of skill, employing accepted principles of diagnosis and treatment Such principles are known in the art, and are set forth, for example, in Braunwald et al., eds., Harrison's Principles of Internal Medicine, 11th Ed., McGraw-Hill, publisher, New York, N.Y. (1987), which is incorporated by reference herein. The pharmaceutical composition may be administered to any animal which may experience the beneficial effects of the composition. Animals receiving the pharmaceutical composition may be humans or other mammals.

The pharmaceutical composition may be administered by any means that achieve their intended purpose. For example, administration may be by parenteral, subcutaneous, intravenous, intradermal, intramuscular, intraperitoneal, transdermal, or buccal routes. Alternatively, or concurrently, administration may be by the oral route. The pharmaceutical compositions may be administered parenterally by bolus injection or by gradual perfusion over time.

The dosage administered may be dependent upon the age, sex, health, and weight of the recipient, kind of concurrent treatment, if any, frequency of treatment, and the nature of the effect desired. The dose ranges for the administration of the pharmaceutical compositions may be large enough to produce the desired effect, whereby, for example, an immune response to the peptide, as measured by DH or antibody production, is achieved, and the autoimmune disease is significantly prevented, suppressed, or treated. The doses may not be so large as to cause adverse side effects, such as unwanted cross reactions, generalized immunosuppression, anaphylactic reactions and the like. The dose for humans may range between about 0.001-25 mg/kg body weight.

The pharmaceutical compositions may further comprise suitable pharmaceutically acceptable carriers comprising excipients and auxiliaries which may facilitate processing of the active compounds into preparations which can be used pharmaceutically. Additives to the pharmaceutical compositions may include the inclusion of an adjuvant, such as alum, chitosan, or other adjuvants known in the art. (See, for example, Warren et al., Ann. Rev. Immunol. 4:369-388 (1986); Chedid, L., Feder. Proc. 45:2531-2560 (1986), which is incorporated herein by reference). The pharmaceutical compositions may also further comprise liposomes to enhance delivery or bioactivity, using methods and compounds known in the art.

The pharmaceutical compositions may also be administered orally in the form of tablets and capsules. The pharmaceutical compositions may also be administered rectally in the form of suppositories, and in the form of solutions for injection or oral introduction.

The pharmaceutical compositions may contain from about 0.001 to about 99 percent, or from about 0.01 to about 95 percent of active compound(s), together with the excipient. Suitable excipients may be fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Other pharmaceutical preparations which can be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds may be dissolved or suspended in suitable liquids, such as fatty oils, or liquid paraffin. In addition, stabilizers may be added.

Pharmaceutical preparations which may be used rectally include, for example, suppositories, which consist of a combination of one or more of the active compounds with a suppository base. Suitable suppository bases may be, for example, natural or synthetic triglycerides, or paraffin hydrocarbons. In addition, gelatin rectal capsules may be used which consist of a combination of the active compounds with a base. Possible base materials include, for example, liquid triglycerides, polyethylene glycols, or paraffin hydrocarbons.

Suitable formulations for parenteral administration include aqueous solutions of the peptide or antibody in water-soluble form, for example, water-soluble salts. In addition, suspensions of the peptide or antibody as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. The suspension may also contain stabilizers.

The peptide and antibody may be formulated using conventional pharmaceutically acceptable parenteral vehicles for administration by injection. These vehicles may be nontoxic and therapeutic, and a number of formulations are set forth in Remington's Pharmaceutical Sciences, (supra). Nonlimiting examples of excipients are water, saline, Ringer's solution, dextrose solution and Hank's balanced salt solution. Pharmaceutical compositions may also contain minor amounts of additives such as substances that maintain isotonicity, physiological pH, and stability.

The peptide and antibody may be formulated in purified form substantially free of aggregates and other materials, at concentrations including about 1.0 ng/ml to 100 mg/ml.

Effective doses of the peptide and antibody for use in preventing, suppressing, or treating an autoimmune disease may be in the range of about 1 ng to 100 mg/kg body weight. The dose range may also be between about 10 ng and 10 mg/kg. The dose range may also be between about 100 ng and 1 mg/kg.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The detection of DNA hybrid products was performed using the Digoxigenin Luminescent Detection Kit® according to the manufacturer's instruction (Boehringer Mannheim, Indianapolis, Ind.). The membrane was then exposed to X-ray film for 15-30 min at room temperature.

Of the 20 tested sequences, three CDR3-encoded sequences were detected in a high percentage of MS-derived specimens as opposed to control specimens. Table 1 indicates the Genbank Accession Number for the TCR genes comprising each of the three detected CDR3-encoded sequences, as well as the nucleotide and amino acid sequence of the CDR3 region for each sequence. Table 2 indicates the total percentage of positive detection of the CDR3-encoded sequences in MS-derived and control PBL specimens.

TABLE 1

CDR3 sequences specific for MBP83-99

| Genbank Accession | V gene | CDR3 Sequence | |
|---|---|---|---|
| MS2002-DH | BV17 | gcc agt agt act gac tgg agc | (SEQ ID NO:1) |
| | | A   S   S   T   D   W   S | (SEQ ID NO:4) |
| MS2002-18 | BV5.2 | agc agc ttg agg ggg gcg cta aac att | (SEQ ID NO:2) |
| | | S   S   L   R   G   A   L   N   I | (SEQ ID NO:5) |
| MSFRANS1 E3 | BV9 | agc agc caa gat cgt ttt tgg | (SEQ ID NO:3) |
| | | A   S   Q   D   R   F   W | (SEQ ID NO:6) |

EXAMPLE 1

T Cell Receptor Vβ-Dβ-Jβ DNA Sequences Identified In Patients With MS

A set of 20 CDR3 sequences of MBP-reactive T cells recognizing the 83-99 immunodominant epitope of MBP were selected from Genbank. In order to determine whether any of the 20 sequences were commonly expressed, peripheral blood lymphocyte specimens from 40 MS patients and 15 control individuals were screened using a two-step RT-PCR and primers based on the RT-PCR detection described in U.S. Pat. No. 6,303,314 (Zhang), which is hereby incorporated in its entirety.

Briefly, total RNA is extracted from T cells from MS patients and controls using RNeasy mini kit (Qiagen, Santa Clarita, Calif.). First-strand cDNA reverse transcribed from total RNA is subject to a first round of PCR amplification using a Vβ-family specific primer and a Cβ primer, followed by a second round of nested or semi-nested PCR using a Vβ-Dβ-Jβ primer and a Cβ primer. The amplified PCR products were electrophoretically separated in a 1% agarose gel and transferred to a positively charged nylon membrane (Boehringer Mannheim, Indianapolis, Ind.) using vacuum blot (Bio-Rad, Hercules, Calif.) at 5 mHg for 90 min. DNA was fixed onto the membrane by 3 min-exposure to UV crosslinking and prehybridized at 68° C. for at least 1 hour. 0.1 mg/ml of poly (A) was added to prehybridization solution (5×SSC, 1% blocking solution, 0.1% N-laurylsarcosine, 0.02% SDS) to reduce non-specific binding of the probe to non-target DNA. Hybridization temperature and washing conditions were optimized according to different CDR3-specific probes to ensure a stringent hybridization condition. Hybridization was carried out in a buffer containing 5×SSC, 1% blocking solution, 0.1% N-Lauroylsarkosine, 0.02% SDS, and 0.3 pmol/ml of a digoxigenin-labeled probe specific for the nucleotide sequence encoding the CDR3 region.

TABLE 2

| Percentage of positive detection of CDR3 DNA | | |
|---|---|---|
| Genbank Accession | % in MS patients | % in controls |
| MS2002-DH | 57.5% | 33% |
| MS2002-18 | 50% | 6.7% |
| MSFRANS1 E3 | 80% | 20% |

The results in Table 2 are surprising, because a number of studies do not support a preferential use of particular Vβ-Dβ-Jβ gene products. For example, the LGARAGLTY (SEQ ID NO: 7) motif described in U.S. Pat. No. 6,303,314 (Zhang) is only found in some individuals. Rather, MBP autoreactive T-cell clones typically show a heterogeneous pattern of the Vβ-Dβ-Jβ gene usage that is relatively restricted in individuals. It was generally believed in the art that the heterogeneity of Vβ-Dβ-Jβ gene usage would significantly impair the feasibility of using a peptide vaccine based approach to eliminate pathogenic autoreactive T cells therapeutically. The results herein describe for the first time that a vaccine based on one or more peptides may prove beneficial in the elimination of pathogenic autoreactive T cells.

EXAMPLE 2

Preparation of Anti-MBP-Reactive T Cell Receptor Monoclonal Antibodies

The procedure for preparing a hybrid cell line which produces anti-MBP-reactive T cell receptor monoclonal antibodies involves fusion of myeloma cells of a BALB/c mouse with the spleen cells of BALB/c mice primed with peptide motifs from specific MBP-reactive T cell receptor protein.

1. Preparation of Spleen Cells for Fusion

The peptide motifs from specific MBP-reactive T cell receptors may be isolated from purified recombinant T cell receptors, or by peptide synthesis. The peptide motif is purified to greater than 95% purity and used to immunize adult BALB/c or C57B46 male mice by subcutaneous administration of about 30 ug emulsified in Freund's complete adjuvant. The mouse was reimmunized 2 weeks later with a further inoculation of the peptide motif in incomplete adjuvant given subcutaneously. After an additional 2-6 weeks, 20-40 ug of the peptide motif is administered intravenously, and 2-4 days later the mice are sacrificed and a spleen cell suspension is prepared in the manner taught by Gefter, et al., Somatic Cell Genetics 3:231, 1977. Red blood cells are lysed for incubation of 15 minutes at 40° C. in $NH_4Cl$ (0.83%). The resulting cell suspension is washed by centrifugation (800×g) through heat-inactivated calf serum followed by centrifugation in protein-free medium (RRMI 1640, buffered with 7.5 mM HEPES, pH 7.2).

2. Preparation of Myeloma Cells for Fusion

Myeloma cells derived from the P3U1 line and deficient in HPRT (E.C2.4.2.8) as described by Yelton, et al., Curr. Top. Microbiol. Immunal. 81:1-7 (1978), are maintained in Eagle's minimum essential medium (MEM) containing 10% fetal calf and 15% horse serum. The growth of myeloma cells is inhibited by selective hypoxanthine-aminopeterin-thymidine (HAT) medium.

3. Production of Hybrids

Production of hybrids is accomplished by mixing $10^7$ BALB/c myeloma cells with $10^8$ spleen cells obtained from the peptide motif immunized BALB/c or C57B1/6 mice. The cell mixture is centrifuged at 800×g and the cells are resuspended for fusion in a 50% solution (w/v) of polyethylene glycol (PEG 1000) diluted in minimum essential medium (MEM) without serum following the procedure described by Gefter et al. (1977). The resulting hybridoma cells are cloned in hypoxanthine-aminopeterin-thymidine (HAT) medium by limiting dilution as described by Galfre and Milstein Meth. Enzymol. 73:3, 1975. Hybridoma cell lines are selected which produces an antibody which recognizes the peptide motif.

4. Testing of the Clones for Production of MBP-Reactive T Cell Receptor Antibody Linbro (Flow Lab) microtiter 96 well plates are coated with 50-100 µg of peptide motif or T cell receptor protein and incubated at 20° C. overnight. After washing the wells three times with 0.1 M Tris (pH 7.5)—1% nonidet P-40, containing 5% Carnation Instant Milk and 0.085 sodium azide, 0.05. ml of the culture supernatants are added and incubated at 40° C. overnight. The supernatant is removed after washing three times with RIA buffer and the antibodies are detected using the Hybridoma Screening Kit (Bethesda Research Labs). Controls for non-specific binding are included by omitting either the second antibody or the culture supernatant.

The invention now being fully described, it will be apparent to one of ordinary skill in the art that many changes and modifications can be made thereto without departing from the spirit or scope of the invention as set forth below.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 3

Identification of an Effective Peptide-Based Vaccine for Treatment of MS Patients The inclusion criteria for this trial is patients with clinically definite MS for at least two years, baseline expanded disability scale score (EDSS) of 1.5 to 6.5 for RR-MS and 4.0 to 8.0 for patients with secondary progressive MS (SP-MS), and at least one exacerbation in the past two years prior to study entry for the releasing-remitting MS (RR-MS) cohort. The patients are not to have taken any immunosuppressive drugs, including steroids, at least three months prior to enrolling in the study. Steroids are permitted during the study if an exacerbation occurs. Symptomatic treatments for fatigue, spasticity and bladder complaints are not prohibited. The patients are to be tested for the presence of autoreactive T cells with TCRs comprising SEQ ID NOS: 4, 5, 6, 10, or the CDR sequences disclosed in U.S. Pat. No. 5,614,192 (Vandenbark).

Vaccines are prepared comprising an immunogenically effective amount of peptide-based antigens with sequences comprising SEQ ID NOS: 4, 5, 6 or 10, or sequences derived therefrom. A total of 15 vaccines are tested as follows; (i) one of the four antigens (4 total), (ii) combinations of two of the four antigens (6 total), (iii) combination of three of the four antigens (4 total), and (iv) combination of four of the antigens (1 total). Each patient receives three subcutaneous injections of one of the test vaccines at two-month intervals.

Patients are then observed for time to onset of confirmed progression of disability, EDSS, rate of relapse and MRI lesion activities. The results are compared with the patient's own pre-treatment course as well as the placebo arms of two recent clinical trials in RR-MS and SP-MS patients, which served as an estimate of the natural history of MS (Jacobs et al., 1996), European Study Group, 1998). Time to progression is determined by an increase of at least 1.0 on the EDSS (Poser et al., 1983) persisting for at least 2 months. On-study exacerbations is defined by the appearance of new neurological symptoms or worsening of pre-existing neurological symptoms lasting for at least 48 hours, accompanied by objective change on neurological examination (worsening of at least 0.5 point on EDSS). Patients are instructed to report events between the scheduled regular visits, and are examined by a neurologist if symptoms suggested an exacerbation. Safety assessments include adverse events, vital signs and physical examinations at regular visits. The differences in the clinical variables in study patients before and after peptide-based vaccination is analyzed using the Wilcoxon's rank-sum test.

EXAMPLE 4

Treatment of MS Patients Using a Peptide-Based Vaccine

Vaccines identified in Example 3 that are effective at slowing the progression of the clinical symptoms of MS are administered to MS patients. The patients receiving vaccine treatment may be suffering from MS of any duration and may be diagnosed by any known criteria.

What is claimed is:

1. A vaccine comprising a first peptide, wherein the first peptide comprises the sequence of SEQ ID NO:4, and optionally a pharmaceutically acceptable carrier.

2. The vaccine of claim 1, wherein the peptide consists of the sequence of SEQ ID NO:4.

3. A peptide comprising the sequence of SEQ ID NO:4.

4. The vaccine of claim 1 further comprising a second peptide, wherein the sequence of the second peptide comprises the sequence of SEQ ID NO:5.

5. The vaccine of claim 1 further comprising a second peptide, wherein the sequence of the second peptide comprises the sequence of SEQ ID NO:6.

6. The vaccine of claim 1 further comprising a second peptide and a third peptide, wherein the sequence of the second peptide comprises the sequence of SEQ ID NO:5 and wherein the sequence of the third peptide comprises the sequence of SEQ ID NO:6.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Homo sapiens

<400> SEQUENCE: 1
gccagtagta ctgactggag c                                              21

<210> SEQ ID NO 2
<211> LENGTH: 27
<212> TYPE: DNA
<213> ORGANISM: Homo sapiens

<400> SEQUENCE: 2
agcagcttga gggggggcgct aaacatt                                        27

<210> SEQ ID NO 3
<211> LENGTH: 21
<212> TYPE: DNA
<213> ORGANISM: Homo sapiens

<400> SEQUENCE: 3
agcagccaag atcgttttttg g                                             21

<210> SEQ ID NO 4
<211> LENGTH: 7
<212> TYPE: PRT
<213> ORGANISM: Homo sapiens

<400> SEQUENCE: 4

Ala Ser Ser Thr Asp Trp Ser
1               5

<210> SEQ ID NO 5
<211> LENGTH: 9
<212> TYPE: PRT
<213> ORGANISM: Homo sapiens

<400> SEQUENCE: 5

Ser Ser Leu Arg Gly Ala Leu Asn Ile
1               5

<210> SEQ ID NO 6
<211> LENGTH: 7
<212> TYPE: PRT
<213> ORGANISM: Homo sapiens

<400> SEQUENCE: 6

Ala Ser Gln Asp Arg Phe Trp
1               5

<210> SEQ ID NO 7
<211> LENGTH: 8
<212> TYPE: PRT
<213> ORGANISM: Homo sapiens

<400> SEQUENCE: 7

Leu Gly Arg Ala Gly Leu Thr Tyr
1               5